(12) United States Patent
Tanaka et al.

(10) Patent No.: US 12,105,054 B2
(45) Date of Patent: Oct. 1, 2024

(54) PHOTOACOUSTIC ANALYSIS METHOD AND DEVICE

(71) Applicant: Nippon Telegraph and Telephone Corporation, Tokyo (JP)

(72) Inventors: Yujiro Tanaka, Tokyo (JP); Takuro Tajima, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 330 days.

(21) Appl. No.: 17/775,927

(22) PCT Filed: Nov. 15, 2019

(86) PCT No.: PCT/JP2019/044864
§ 371 (c)(1),
(2) Date: May 11, 2022

(87) PCT Pub. No.: WO2021/095230
PCT Pub. Date: May 20, 2021

(65) Prior Publication Data
US 2022/0390417 A1    Dec. 8, 2022

(51) Int. Cl.
*G01N 29/24*    (2006.01)
(52) U.S. Cl.
CPC ............................... *G01N 29/2418* (2013.01)

(58) Field of Classification Search
CPC ..... G01N 29/2418; G01N 2291/02809; G01N 21/00; G01N 29/12; A61B 5/0095
See application file for complete search history.

(56) References Cited

U.S. PATENT DOCUMENTS

2021/0121105 A1*  4/2021  Ajito .................. A61B 5/14532
2021/0177267 A1*  6/2021  Tanaka ............... A61B 5/14532

FOREIGN PATENT DOCUMENTS

JP           2017217203 A      12/2017

* cited by examiner

*Primary Examiner* — Tarun Sinha
(74) *Attorney, Agent, or Firm* — Slater Matsil, LLP

(57) ABSTRACT

A light source that emits beam light, a beam shaping unit that shapes the beam light, and a pulse control unit that forms the beam light into pulse light are included. The light source emits beam light that has a wavelength that is to be absorbed by a measurement-target substance. The pulse control unit forms beam light that is emitted from the light source and with which a measurement-target part is irradiated, into pulse light that has a preset frequency and has a pulse width that is a reciprocal of twice the frequency. The beam shaping unit shapes the beam light so that a beam radius of the beam light that is emitted from the light source and with which the measurement-target part is to be irradiated is equal to a value obtained by dividing a speed of sound by $\pi \times f$, where f denotes the frequency.

8 Claims, 5 Drawing Sheets

| Modulation | Harmonic | Pulse |
|---|---|---|
| Image |  |  |
| Phase align Single frequency | △ | △ |
| PA source interference | × | △ |
| PA conversion | × | ○ |

PHOTOACOUSTIC ANALYSIS METHOD AND DEVICE

CROSS-REFERENCE TO RELATED APPLICATIONS

This application is a national phase entry of PCT Application No. PCT/JP2019/044864, filed on Nov. 15, 2019, which application is hereby incorporated herein by reference.

TECHNICAL FIELD

The present invention relates to a photoacoustic analysis method and apparatus that utilize a photoacoustic method.

BACKGROUND

Spatial information regarding interstitial fluid components (for example, sugars such as glucose) and blood vessels is useful for early detection of diabetes and malignant neoplasms. The photoacoustic method is a method for grasping the light absorption characteristics of a substance by utilizing the fact that when a substance is irradiated with light, a sound wave is generated due to local thermal expansion according to the absorption wavelength range of the substance (see PTL 1). In addition, the photoacoustic method is characterized in that a sound wave generated as described above is a kind of ultrasonic wave and has a longer wavelength than light, and therefore such sound wave is unlikely to be affected by scattering caused by a measurement target. Because of this characteristic, the photoacoustic method is attracting attention as a technique for visualizing the light absorption characteristics of a measurement target in a measurement-target part that causes a high degree of scattering, such as a living body.

CITATION LIST

Patent Literature

[PTL 1] Japanese Patent Application Publication No. 2017-217203.

SUMMARY

Technical Problem

In general, in a measurement according to a photoacoustic method, light generated by a semiconductor laser is focused to a spot, scanning is performed with the light spot of the focused light so as to irradiate the measurement-target part that includes the measurement target with the light spot, and an ultrasonic wave (a photoacoustic wave) generated at each position irradiated with the scanning light spot (beam light) are detected using an acoustic sensor or the like. If an absorbent substance is present at any of the irradiated positions, an ultrasonic wave is generated at the position as a result of scanning performed with the beam light. By measuring such an ultrasonic wave, it is possible to measure (analyze) the light absorption characteristics of the measurement target. In addition, in a measurement of the blood glucose level in the living body, for example, it is necessary to obtain detailed light absorption characteristics, and therefore, light irradiation is consecutively performed at a constant frequency to generate an ultrasonic wave (a photoacoustic wave), and measurement is performed through lock-in detection with the frequency band being narrowed down using a long time constant.

However, first, this technique requires a resonator to selectively extract the frequency to be measured. With such a configuration that requires an external resonator, the apparatus needs to be complex.

Secondly, when a resonator is not used, it is necessary to resonate an ultrasonic wave in the measurement-target part. However, when light that has entered from the surface of the measurement-target part (arm surface) to the inside of the measurement-target part is to be resonated internally, it is difficult to perform measure in a part with a structure such as a bone, and it is inevitable to perform measurement on an extremely limited part such as an ear canal (see FIG. 9).

Thirdly, the component to be measured regarding blood glucose or the like has a small light contrast inside the measurement-target part, and therefore the light spot that generates an ultrasonic wave, i.e., the sound source region (the sound source distribution region) is the same region as the distribution region in which light is absorbed, and a complex wide-band ultrasonic wave is generated. In such measurements, it is necessary to use a wide-band transducer because of band-dependent distance attenuation and ultrasonic wave attenuation due to interference caused by phase differences.

However, with a wide-band transducer, it is not easy to increase sensitivity, and in order to perform measurement with high sensitivity, it is important to use a narrow-band transducer with which sensitivity can be increased. However, as described above, conventionally, there is a problem that a narrow-band transducer cannot be used as a measuring device and it is not easy to perform an analysis using a photoacoustic method, with high sensitivity.

Embodiments of the present invention have been made to solve the above-described problems, and an object thereof is to perform an analysis using a photoacoustic method, with high sensitivity.

Means for Solving the Problem

A photoacoustic analysis method according to embodiments of the present invention is a photoacoustic analysis method through which a measurement-target part is irradiated with beam light that has a wavelength that is to be absorbed by a measurement-target substance, and that has been generated by a light source, and a measuring unit measures a photoacoustic signal generated in a direction that is orthogonal to an optical axis of the beam light, from the measurement-target part irradiated with the beam light, the photoacoustic analysis method including: a first step of forming beam light into pulse light that has a frequency of a photoacoustic signal that can be measured by a measuring unit and has a pulse width that is a reciprocal of twice the frequency; a second step of shaping the beam light so that a beam radius of the beam light is equal to a value obtained by dividing a speed of sound by $\pi \times f$, where f denotes the frequency; a third step of irradiating a measurement-target part with the beam light formed into the pulse light in the first step and shaped in the second step; and a fourth step of measuring a photoacoustic signal generated in a direction that is orthogonal to an optical axis of the beam light, from the measurement-target part irradiated with the beam light in the third step, using the measuring unit.

A photoacoustic analysis apparatus according to embodiments of the present invention includes: a light source that emits beam light that has a wavelength that is to be absorbed by a measurement-target substance; a pulse control unit that forms the beam light that is emitted from the light source and with which a measurement-target part is to be irradiated, into pulse light that has a preset frequency and has a pulse width that is a reciprocal of twice the frequency; a beam shaping unit that shapes the beam light so that a beam radius of the beam light that is emitted from the light source and with which the measurement-target part is to be irradiated is equal to a value obtained by dividing a speed of sound by π×f, where f denotes the frequency; and a measuring unit that is enabled to measure a photoacoustic signal of a frequency, and measures a photoacoustic signal generated in a direction that is orthogonal to an optical axis of the beam light, from the measurement-target part irradiated with the beam light that has been formed into the pulse light by the pulse control unit and that has been shaped by the beam shaping unit.

EFFECTS OF EMBODIMENTS OF THE INVENTION

As described above, according to embodiments of the present invention, beam light is formed into pulse light that has the frequency of a photoacoustic signal that can be measured by the measuring unit and has a pulse width that is the reciprocal of twice the frequency, and is shaped so that the beam radius of the beam light is equal to the value obtained by dividing the speed of sound by π×f, where f denotes the frequency. Therefore, it is possible to perform an analysis using a photoacoustic method, with high sensitivity.

DETAILED DESCRIPTION OF ILLUSTRATIVE EMBODIMENTS

Figure 1:
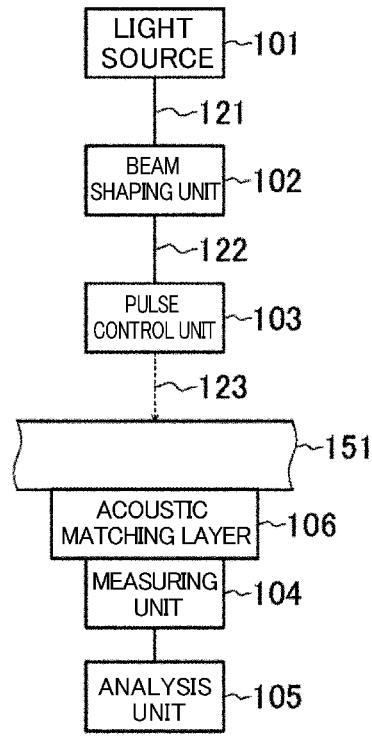
FIG. 1 is a configuration diagram showing a configuration of a photoacoustic analysis apparatus according to an embodiment of the present invention.

The following describes a photoacoustic analysis apparatus according to an embodiment of the present invention with reference to FIG. 1. The photoacoustic analysis apparatus includes a light source 101 that emits beam light, a beam shaping unit 102 that shapes the beam light, a pulse control unit 103 that forms the beam light into pulse light, and a measuring unit 104 that measures a photoacoustic signal.

The light source 101 emits beam light 121 that has a wavelength that is to be absorbed by a measurement-target substance. The light source 101 emits beam light 121 that has a wavelength that is to be absorbed by glucose that is a measurement-target substance. The light source 101 may be constituted by a semiconductor laser, for example.

The pulse control unit 103 forms beam light 123 that is emitted from the light source 101 and with which a measurement-target part 151 is irradiated, into pulse light that has a preset frequency and has a pulse width that is a reciprocal of twice the frequency. The beam shaping unit 102 shapes the beam light 121 so that the beam radius of the beam light 123, which is emitted from the light source 101 and with which the measurement-target part 151 is irradiated, is equal to a value obtained by dividing the speed of sound by π×f, where f denotes the frequency. For example, the beam shaping unit 102 shapes the beam light 121 into shaped beam light 122, and the pulse control unit 103 forms beam light 123 by forming the shaped beam light 122 into pulse light. Alternatively, for example, the pulse control unit 103 may form the beam light 121 into pulse light, and the beam shaping unit 102 may shape the pulse light and irradiate the measurement-target part 151 with the pulse light.

The measuring unit 104 measures the photoacoustic signal that is generated in the direction orthogonal to the optical axis of the beam light from the measurement-target part 151 irradiated with the beam light 123 that has been formed into pulse light by the pulse control unit 103 and shaped by the beam shaping unit 102. The measuring unit 104 may be constituted by a transducer (a narrow-band transducer) that detects a photoacoustic wave that is an ultrasonic wave, and converts it into an electric signal (a photoacoustic signal).

Here, the measuring unit 104 is enabled to measure a photoacoustic signal of a frequency, and this frequency is set by the beam shaping unit 102 and the pulse control unit 103. Note that, on order to prevent the photoacoustic signal from being reflected between the measurement-target part 151 and the measuring unit 104, an acoustic matching layer 106 that adjusts an acoustic impedance may be provided between the measurement-target part 151 and the measuring unit 104.

In addition, in this photoacoustic analysis apparatus, an analysis unit 105 obtains the characteristics of the substance based on the photoacoustic signal measured by the measuring unit 104. The analysis unit 105 obtains the concentration of the substance based on the photoacoustic signal measured by the measuring unit 104.

Figure 2:
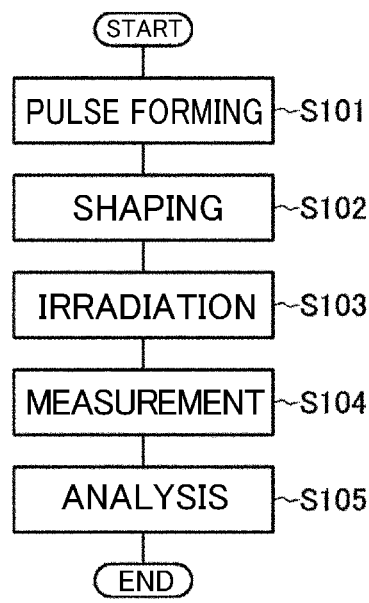
FIG. 2 is a flowchart illustrating a photoacoustic analysis method according to an embodiment of the present invention.

Next, a photoacoustic analysis method according to the embodiment of the present invention will be described with reference to the flowchart in FIG. 2. Through this photoacoustic analysis method, the measurement-target part 151 is irradiated with beam light that has a wavelength that is to be absorbed by the measurement-target substance, and that has been generated by the light source 101, and the measuring unit 104 measures a photoacoustic signal generated in a direction that is orthogonal to the optical axis of the beam light, from the measurement-target part 151 irradiated with the beam light.

First, in a first step S101, the pulse control unit 103 forms beam light into pulse light that has a frequency of a photoacoustic signal that can be measured by the measuring unit 104 and has a pulse width that is a reciprocal of twice the frequency. In a second step S1o2, the beam light is shaped by the beam shaping unit 102 so that a beam radius of the beam light is equal to a value obtained by dividing the speed of sound by π×f, where f denotes the frequency. Note that the first step S101 may be carried out after the second step S1o2.

Next, in a third step S103, the measurement-target part 151 is irradiated with the beam light formed into the pulse light in the first step S101 and shaped in the second step S1o2. Thereafter, in a fourth step S104, a photoacoustic signal generated in a direction that is orthogonal to the optical axis of the beam light, from the measurement-target part 151 irradiated with the beam light, is measured using the measuring unit 104. Also, in a fifth step S105, the analysis unit 105 obtains the characteristics of the substance (for example, the concentration of the substance) based on the measured photoacoustic signal.

Hereinafter, a more detailed description will be given. As described above, in a state where a complex wide-band photoacoustic wave (ultrasonic wave) is generated through light irradiation, it is necessary to use a wide-band transducer, and it is not possible to increase sensitivity. In order to increase sensitivity, it is important to use a narrow-band transducer. For this purpose, in a measurement using the photoacoustic method, it is important to generate an ultrasonic wave in which energy is collected at a specific frequency, i.e., an ultrasonic wave with a specific frequency, through light irradiation.

Figure 9:
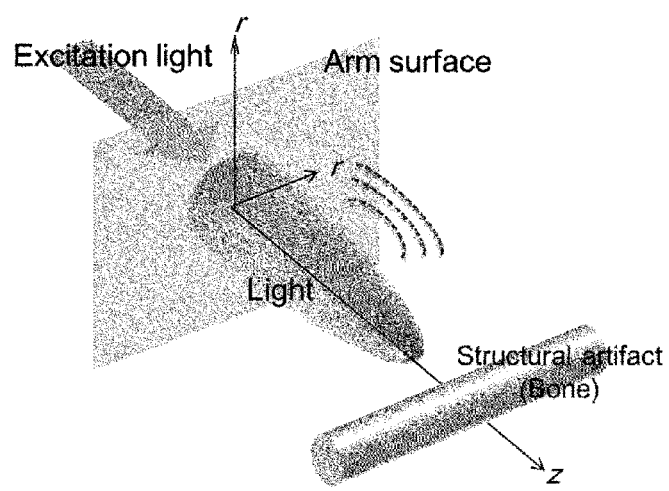
FIG. 9 is an explanatory diagram showing a state of distribution of emitted light, from a surface of a measurement-target part that includes a structure such as a bone.

Here, when the light absorption contrast of the measurement target in the measurement-target part is small, the collimated light (beam light) corresponds to the light absorption coefficient according to Beer's law and is gradually absorbed from the surface of the measurement-target part. The distribution thereof will be as indicated by Formula (i) (see FIG. 9). The generation of an ultrasonic wave is proportional to the absorption of light as indicated by Formula (2).

Math 1

$$F = F_0 \exp\left(-\frac{2r^2}{w^2}\right) \exp(-\mu z) \quad (1)$$

$$\text{Ultrasonic Wave } P = \Gamma \mu F \frac{dI}{dt} \quad (2)$$

Γ denotes the Grüneisen coefficient, µ denotes the light absorption coefficient at the measurement target (measurement-target part), F denotes the energy of light, $F_o$ denotes the light energy at the surface of the measurement-target part, w denotes the beam waist (the beam radius), r denotes the distance from the optical axis of the emitted light, z denotes the distance from the surface of the measurement-target part in the optical axis direction, and I denotes the light intensity distribution (the pulse of the pulse) in the time domain.

Figure 10:
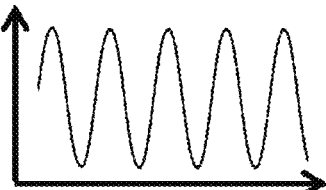
FIG. 10 illustrates Table 1, showing modulation with different waves.
Figure 10:
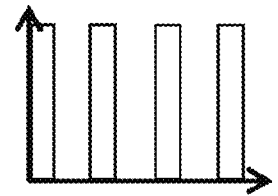

From the above, even if the intensity of the emitted light is modulated into a sinusoidal shape based on the distribution of the ultrasonic source generated through light irradiation, a complex wavefront and various frequency components are generated due to the interference between the ultrasonic source and the propagating ultrasonic waves, and attenuation occurs again. In addition, the sound pressure of an ultrasonic wave generated due to the photoacoustic effect is proportional to the time derivative of the intensity of light. For this reason, modulation with a sine wave (Harmonic), which changes gently, is disadvantageous in terms of conversion efficiency (see Table 1 of FIG. 10). Note that, Table 1 shows the results of determination regarding an advantage and a disadvantage in the order of "○", "Δ", and "x".

Therefore, in embodiments of the present invention, the measurement target (measurement-target part) is irradiated with pulsed light (beam light) (see the right side of Table 1).

Figure 3:
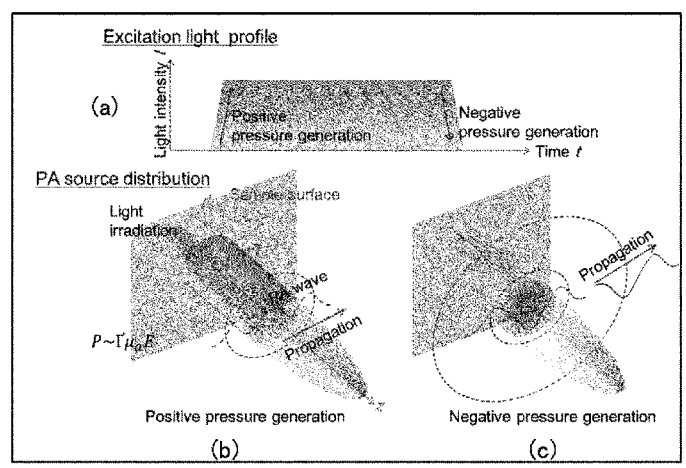
FIG. 3 is an explanatory diagram illustrating two pulses generated when an optical pulse longer than a stress confinement time is emitted.

Next, regarding the photoacoustic wave, the light energy irradiated within the stress confinement time (representative length/speed of sound, in this case, the representative length is the diameter of the beam) is emitted as an ultrasonic wave. The stress confinement time is the time until the stress generated in the measurement-target part as a result of irradiation with beam light is transmitted in the direction orthogonal to the optical axis of the beam light in the region irradiated with the beam light. Therefore, as shown in FIG. 3(a), when an optical pulse longer than the stress confinement time is emitted, two pulses are generated as shown in FIG. 3(b) and FIG. 3(c). As shown in Formula (2), the generated sound pressure is proportional to the change in light intensity over time, and therefore the two generated waves have a symmetrical sound pressure distribution with inverted signs.

Therefore, in order to set the ultrasonic wave generated by the photoacoustic effect to has a specific frequency f to increase the sensitivity of measurement, an optical pulse that has a pulse width of ½f is to be emitted at the frequency f. By combining the positive and negative waves generated as a result of irradiation with light pulses that have such a long pulse width, it is possible to eliminate the even-order harmonics generated when the repetition of nanosecond pulses is used. However, at this stage, the resulting ultrasonic waves still have a wide frequency band.

Next, the band of the ultrasonic wave obtained with the even-order harmonics set to zero as described above is further narrowed to be closer to a sine wave as shown below.

Figure 4:
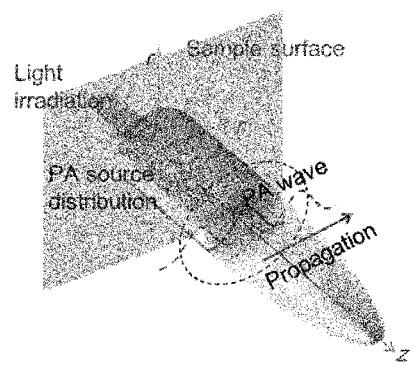
FIG. 4 is an explanatory diagram illustrating a state in which emitted beam light enters a measurement-target part from the surface thereof and an intensity distribution of the light is immediately converted into a sound source distribution.

As described earlier, when the emitted beam light (Light irradiation) penetrates into the inside from the surface of the measurement-target part (Sample surface), the light intensity distribution is immediately converted to the sound source distribution (see FIG. 4). The sound source distribution, which is the distribution of a photoacoustic wave (PA wave) generated through this photoacoustic (PA) effect and propagating in the orthogonal direction (Propagation) away from the optical axis (z axis), can be expressed as "$\exp(-2r^2/w^2)\exp(-\mu z) \ldots (3)$".

Here, attention is paid to the sound pressure distribution in the direction orthogonal to the optical axis represented by "$\exp(-2r^2/w^2) \ldots (4)$" in Formula (3). When this Formula (4) is subjected to Taylor series expansion with respect to the distance r in the direction orthogonal to the optical axis, "$1-(2r^2)/(w^2) \ldots (5)$" can be obtained.

The ultrasonic wave of the frequency to be generated can be expressed as "$\exp\{i2\pi f(r/c)\} \ldots (6)$". Note that "i" represents an imaginary unit. Also, "c" represents the speed of sound. When this Formula (6) is subjected to Taylor series expansion with respect to the distance r in the direction orthogonal to the optical axis, "1-½{2πf(r/c)}² ... (7)" can be obtained.

Figure 5:
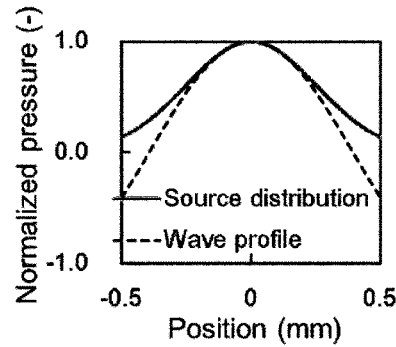
FIG. 5 is a characteristic diagram showing a sound source distribution (a solid line), and a sound pressure distribution (a dotted line) of a propagating ultrasonic wave.
Figure 6:
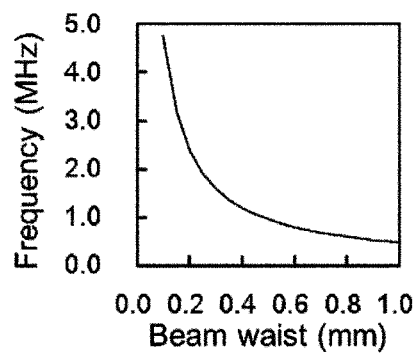
FIG. 6 is a characteristic diagram showing an example of a relationship between a frequency f of an ultras at is to be generated and a beam waist w of light.

Here, as shown in FIG. 5, the sound source distribution (a solid line) and the sound pressure distribution (a dotted line) of the propagating ultrasonic waves can be approximated very well, and Formula (6) and Formula (7) can be regarded as being equal to each other. As a result, "f=c/(πw) ... (8)" indicating the relationship between the frequency f of the ultrasonic wave to be generated and the light beam waist w can be obtained. From the relationship indicated by Formula (8), the beam waist (beam radius) and the appropriate pulse width can be determined according to the ultrasonic wave of the frequency to be generated through the photoacoustic effect. FIG. 6 shows an example of this relationship.

Figure 7:
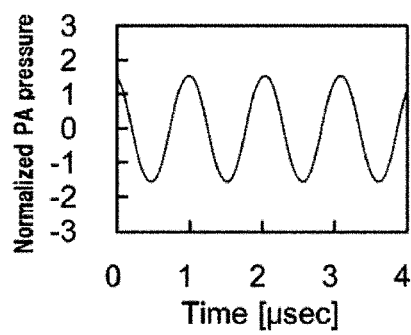
FIG. 7 is a characteristic diagram showing a waveform of an ultrasonic wave (a photoacoustic wave) of 955 kHz measured by a measuring unit 104 when the beam waist is formed to be 0.5 mm by a beam forming unit 102 and light is emitted by a pulse control unit 103 with a pulse width of 0.52 μsec.

FIG. 7 shows the waveform of the 955 kHz ultrasonic wave (photoacoustic wave) measured by the measuring unit 104 when the beam shaping unit 102 shapes the beam waist to be 0.5 mm and the pulse control unit 103 emits light with a pulse width of 0.52 μsec. When the concentration of the component to be measured changes and the light absorption coefficient changes in the state where the ultrasonic wave is obtained in this way, the amplitude of the ultrasonic wave changes according to the change in the concentration. Based on this change, it is possible to obtain the concentration of the substance to be measured, using the analysis unit 105.

Figure 8:
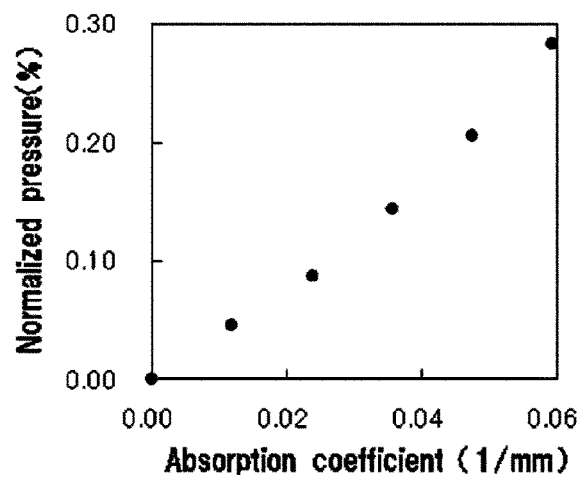
FIG. 8 is a characteristic diagram showing a relationship between a signal and a light absorption coefficient when an ultrasonic wave (a photoacoustic wave) measured according to an embodiment is subjected to lock-in detection.

FIG. 8 shows the relationship between the signal and the light absorption coefficient when the above-described ultrasonic wave is subjected to lock-in detection. S1 denotes a signal after the component concentration has changed with reference to an initial signal S0, and the vertical axis indicates a value standardized by (S1-S0)/S0. It can be seen that an ultrasonic wave of a specific frequency can be generated without using a resonator or the like, a linear response with respect to the light absorption coefficient of the measurement-target substance can be obtained, and a change in the concentration of the measurement-target component in the measurement-target part can be measured.

As described above, according to embodiments of the present invention, beam light is formed into pulse light that has the frequency of a photoacoustic signal that can be measured by the measuring unit and has a pulse width that is the reciprocal of twice the frequency, and is shaped so that the beam radius of the beam light is equal to the value obtained by dividing the speed of sound by π×f, where f denotes the frequency. Therefore, it is possible to use, for example, a narrow-band transducer to perform measurement. As described above, it is possible to use a narrow-band transducer that can increase sensitivity. Therefore, according to the present invention, it is possible to perform analysis using the photoacoustic method, with high sensitivity.

Note that the present invention is not limited to the embodiment described above, and many modifications and combinations can be carried out by a person having ordinary knowledge in the art, within the technical idea of the present invention.

REFERENCE SIGNS LIST

101 Light source
102 Beam shaping unit
103 Pulse control unit
104 Measuring unit
105 Analysis unit
106 Acoustic matching layer
121 Beam light
122 Shaped beam light
123 Beam light
151 Measurement-target part.

The invention claimed is:

1. A photoacoustic analysis method comprising:
   a first step of forming beam light into pulse light that has a frequency of a photoacoustic signal that can be measured by a measuring device and has a pulse width that is a reciprocal of twice the frequency of the photoacoustic signal that can be measured by the measuring device, the beam light having a wavelength that is to be absorbed by a measurement-target substance;
   a second step of shaping the beam light so that a beam radius of the beam light is equal to a value obtained by dividing a speed of sound by π×f, where f denotes the frequency of the photoacoustic signal that can be measured by the measuring device;
   a third step of irradiating a measurement-target part with the beam light formed into the pulse light in the first step and shaped in the second step; and
   a fourth step of measuring a photoacoustic signal generated in a direction that is orthogonal to an optical axis of the beam light, from the measurement-target part irradiated with the beam light in the third step, using the measuring device.

2. The photoacoustic analysis method according to claim 1, further comprising:
   a fifth step of obtaining characteristics of the measurement-target substance based on the photoacoustic signal measured in the fourth step.

3. The photoacoustic analysis method according to claim 2,
   wherein, in the fifth step, a concentration of the measurement-target substance is obtained based on the photoacoustic signal measured in the fourth step.

4. The photoacoustic analysis method of claim 1, wherein the first step is performed prior to the second step, and the second step of shaping the beam light comprises shaping the pulse light so that the beam radius of the pulse light is equal to the value obtained by dividing the speed of sound by π×f.

5. The photoacoustic analysis method of claim 1, wherein the second step is performed prior to the first step, and the first step of forming the beam light into the pulse light comprises forming the beam light that has been shaped in the second step into the pulse light.

6. A photoacoustic analysis apparatus comprising:
   a light source configured to emit beam light that has a wavelength that is to be absorbed by a measurement-target substance;
   a pulse controller configured to form the beam light emitted from the light source into pulse light that has a preset frequency and has a pulse width that is a reciprocal of twice the preset frequency;
   a beam shaping device configured to shape the beam light from the light source so that a beam radius of the beam light is equal to a value obtained by dividing a speed of sound by π×f, where f denotes the preset frequency; and
   a measuring device configured to measure a photoacoustic signal of the preset frequency, the photoacoustic signal being generated in a direction that is orthogonal to an optical axis of the beam light and being generated from a measurement-target part irradiated with the beam light that has been formed into the pulse light by the pulse controller and that has been shaped by the beam shaping device.

7. The photoacoustic analysis apparatus according to claim 6, further comprising:
   an analyzer configured to obtain characteristics of the substance based on the photoacoustic signal measured by the measuring device.

8. The photoacoustic analysis apparatus according to claim 7,
   wherein the analyzer is configured to obtain a concentration of the substance based on the photoacoustic signal measured by the measuring device.

* * * * *